United States Patent
Logier et al.

(10) Patent No.: US 8,352,020 B2
(45) Date of Patent: Jan. 8, 2013

(54) METHOD FOR PROCESSING A SERIES OF CARDIAC RHYTHM SIGNALS (RR) AND THE USE THEREOF FOR ANALYSING A CARDIAC RHYTHM VARIABILITY, IN PARTICULAR FOR ASSESSING A PATIENT'S PAIN OR STRESS

(75) Inventors: Régis Logier, Béthune (FR); Mathieu Jeanne, Lille (FR); Benoît Tavernier, Lambersart (FR)

(73) Assignees: Centre Hospitalier Regional Universitaire de Lille, Lille (FR); Uiversite de Droite Et de la Sante de Lille II, Lille (FR)

( * ) Notice: Subject to any disclaimer, the term of this patent is extended or adjusted under 35 U.S.C. 154(b) by 915 days.

(21) Appl. No.: 11/663,166

(22) PCT Filed: Aug. 9, 2005

(86) PCT No.: PCT/FR2005/002056
§ 371 (c)(1),
(2), (4) Date: Jun. 11, 2007

(87) PCT Pub. No.: WO2006/032739
PCT Pub. Date: Mar. 30, 2006

(65) Prior Publication Data
US 2008/0132801 A1 Jun. 5, 2008

(30) Foreign Application Priority Data
Sep. 20, 2004 (EP) ..................................... 04370029

(51) Int. Cl.
*A61B 5/0456* (2006.01)

(52) U.S. Cl. ........................................................ 600/521
(58) Field of Classification Search ..... 600/481/509/521
See application file for complete search history.

(56) References Cited

U.S. PATENT DOCUMENTS

| 4,802,491 A * | 2/1989 | Cohen et al. ................... 600/515 |
| 5,148,812 A * | 9/1992 | Verrier et al. .................. 600/517 |
| 5,341,811 A | 8/1994 | Cano et al. |
| 5,458,115 A * | 10/1995 | Sivard et al. ................... 600/521 |
| 6,882,883 B2 * | 4/2005 | Condie et al. ................... 607/11 |
| 7,502,643 B2 * | 3/2009 | Farringdon et al. ........... 600/509 |
| 2002/0128563 A1 * | 9/2002 | Carlson et al. ................ 600/509 |
| 2003/0055343 A1 * | 3/2003 | Korhonen ..................... 600/481 |

FOREIGN PATENT DOCUMENTS

| WO | 03/057034 A | 7/2003 |
| WO | 03/084396 A1 | 10/2003 |

* cited by examiner

*Primary Examiner* — Carl H Layno
*Assistant Examiner* — Jeremiah Kimball
(74) *Attorney, Agent, or Firm* — Harness, Dickey & Pierce, P.L.C.

(57) ABSTRACT

The inventive method for processing an RR series comprises a plurality of (RR) samples representing time intervals (dti) between two successive heart beats or the inverse (1/dti) of said time intervals consists in selecting (N) (RRi) samples in a main time window having a predetermined length (n), in cutting said main window into (m) subwindows ($F_j$), in calculating an intermediate parameter (A1) for each subwindow ($F_j$) on the basis of the (RRi) samples contained in the subwindow ($F_j$) and in calculating a final parameter as a function of the intermediate parameters ($A_j$). The invention is used for analysing a cardiac rhythm variability, in particular for assessing a patient's pain or stress.

18 Claims, 3 Drawing Sheets

METHOD FOR PROCESSING A SERIES OF CARDIAC RHYTHM SIGNALS (RR) AND THE USE THEREOF FOR ANALYSING A CARDIAC RHYTHM VARIABILITY, IN PARTICULAR FOR ASSESSING A PATIENT'S PAIN OR STRESS

CROSS-REFERENCE TO RELATED APPLICATIONS

This application is a National Stage 371 of International Application No. PCT/FR2005/002056, filed Aug. 9, 2005. This application claims the benefit of FR 04370029.3, filed Sep. 20, 2004. The disclosures of the above applications are incorporated herein by reference.

FIELD OF INVENTION

The invention relates in a general manner to the analysis of the cardiac rhythm variability in a living being, and its uses for assessing pain in a living being, particularly a living being conscious under local anaesthesia of the epidural type, or a living being unconscious under general anaesthesia, and for assessing the stress felt by a living being.

PRIOR ART

From a physiological point of view, the heart of a living being, when isolated from all external influence, contracts automatically at a very regular rate, much like a metronome, due to the action of the sino-atrial node, which generates an independent nerve impulse, and through this action triggers a spontaneous contraction of the cardiac muscle. The heart nevertheless is not isolated, but connected to the autonomic nervous system (ANS) via the parasympathetic and sympathetic nervous systems. This autonomic nervous system has an influence on the heart's activity: the sympathetic system accelerates cardiac rhythm while the parasympathetic system slows it down.

Thus, although it is autonomous to some extent, the heart is subjected to the influences of the autonomic nervous system, which makes it possible in particular for the body of a living being to adapt the cardiac rhythm in function of its needs, while nevertheless remaining within reasonable limits. Consequently, it is clear that the analysis of changes over time in cardiac rhythm, and in particular of cardiac rhythm variations (variation of time interval separating two heart beats) enables important information to be obtained on the activity of the cardiac system, and more particularly on the activity of the autonomic nervous system. Knowledge of the activity of the ANS can be a valuable aid in reaching a diagnosis in numerous clinical situations. On this subject, the following publication can for instance be referred to: Lacroix D, Logier R, Kacet S, Hazard J-R, Dagano J (1992): "Effects of consecutive administration of central and peripheral anticholinergic agents on respiratory sinus arrhythmia in normal subjects", Journal of the Autonomic Nervous System, Vol 39, pp 211-218.

In order to study these cardiac rhythm fluctuations and, as a result, the activity of the ANS, various techniques have been developed since 1970 for the spectral analysis of a signal that represents changes over time in the instantaneous cardiac rhythm (or frequency), which is obtained after sampling an analogue bio-electrical signal, characteristic of the cardiac rhythm of a living being, and hereinafter referred to as a cardiac signal.

The main methods of analysing the variability of cardiac rhythm known to date consist in:

acquiring a cardiac signal, by any invasive or non-invasive means [for instance, the acquisition of an electrocardiographic (ECG) signal by means of an electrocardiograph, or the use of a blood pressure sensor connected to a catheter inserted into an artery, or the use of an infrared pulse sensor, these examples being non-exhaustive], constructing, from this signal, a so-called RR series consisting of a plurality of samples (RRi) representing time intervals between two successive heart beats, and implementing a spectral analysis of the RR series.

More particularly, the spectral analysis of an RR series derived from a cardiac signal is usually implemented in two main stages.

In a first stage, the curve for the spectral density of the RR series is calculated, for instance between 0 and 2 Hz, using various known methods. The most commonly used method consists in calculating the discrete fast Fourier transform of the RR series, in predefined time windows, weighted by means of a predefined weighting window. Depending on the foreseen implementation, this can be a rectangular weighting window or, for instance, a Kaiser, Hamming, Hanning or Bartlett weighting window. Similarly, the calculation time windows can also be predefined and constant, or else the calculation time window can be of a predetermined size but made to slide over time. For instance, the Fourier transform is performed in a sliding time window of 256 seconds, applied to the RR series and subjected to Kaiser weighting to limit the edge effects due to the windowing.

In a second stage, from the spectral density curve obtained at the end of the first stage, the spectral powers (areas below the spectral density curve) are calculated automatically between frequency boundaries that are predetermined and possibly user adjustable. Such spectral power calculations enable quantitative information to be obtained, characteristic of the activity of the Autonomic Nervous System (ANS) and thus constitute a means of investigating and analysing cardiac regulation by the ANS.

The above-described spectral analysis method, however, has several disadvantages.

An RR series is non stationary. Consequently, the application of a Fourier transform on this type of non stationary series yields results that are imprecise, possibly even incorrect, and that cannot be interpreted with certainty. Calculating the spectral density curve by fast Fourier transform (or equivalent) is relatively demanding in terms of computation power and/or computation time, which to date makes this method of spectral analysis unsuitable and difficult to implement in real time, in particular in portable systems.

Similarly, to obtain an acceptable frequency resolution, the fast Fourier transform must be calculated over relatively large time windows (for instance 256s), corresponding to a significant number of samples of the RR series. As a result, this method of spectral analysis is accompanied by a memory effect, which delays the recognition of any change occurring in the RR series.

OBJECTS OF THE INVENTION

As its main object, the present invention proposes a new method of automatically processing an RR series, which mitigates the above-described disadvantages inherent to the prior art methods based on spectral analysis, and which enables the calculation of a quantitative value (parameter) characterising with a high degree of sensitivity the activity of the ANS.

SUMMARY OF THE INVENTION

The method for processing an RR series according to the invention is based on a method of time analysis of the samples ($RR_i$) representing the time intervals ($\delta t_i$) separating two successive heart beats or the inverse ($1/\delta t_i$) of said time intervals.

This method consists in selecting (N) samples ($RR_i$) in a main time window having a predetermined length (n), in cutting said main window into (m) subwindows ($F_j$), in calculating an intermediary parameter ($A_j$) for each subwindow ($F_j$) on the basis of the samples (RRi) contained in the subwindow ($F_j$) and in calculating a final parameter as a function of the intermediary parameters ($A_j$).

The invention has as its second object a system for analysing the variability of the cardiac rhythm, whereby the apparatus comprises means of acquiring an analogue cardiac signal, means of sampling said cardiac signal and means of processing the sampled signal, designed to construct an RR series consisting of a plurality of samples ($RR_i$) representing the time intervals ($\delta t_i$) separating two successive heart beats or the inverse ($1/\delta t_i$) of said time intervals, and to calculate automatically from the series (RR) at least one parameter in accordance with the above-described method for processing an RR series.

The third object of the invention is an analysis method of the variability of the cardiac rhythm of a living being. This method comprises the following main stages:

acquisition of an analogue cardiac signal of the living being, sampling of said cardiac signal and construction of an RR series consisting of a plurality of samples ($RR_i$) representing the time intervals ($\delta t_i$) that separate two successive heart beats or the inverse ($1/\delta t_i$) of said time intervals, processing of the RR series pursuant to the above-described method.

In the present specification, and in particular in the claims, the term "cardiac signal" refers to any physical signal characteristic of the instantaneous cardiac rhythm (or frequency) of the living being. In order to implement the invention, various invasive or non-invasive techniques can be used to acquire said cardiac signal. A known invasive technique, for instance, consists in using a blood pressure sensor connected to a catheter inserted into an artery. Known non-invasive methods (which are to be preferred) include, for instance, the use of an infrared pulse sensor, the use of an ultrasound sensor enabling the measurement of cardiac cycles, of the type of sensor used in cardiotocography, or else the acquisition of an electrocardiographic (ECG) signal. The acquisition of an electrocardiographic (ECG) signal is in practice the most commonly used method, since in addition to its non-invasive character, it enables the acquisition of a more precise cardiac signal than that obtained for example by means of an infrared pulse sensor.

In the present specification, and in particular in the claims, the term "RR series" generally indicates a series of several successive samples ($RR_i$), obtained after sampling an analogue cardiac signal characteristic of the cardiac rhythm of the living being, each sample (RRi) characterising in a general manner a time interval ($\delta t_i$) between two successive heart beats or the inverse ($1/\delta t_i$) of said time interval.

In the preferred embodiment described below with reference to the accompanying drawings, this RR series is more particularly constructed from the R waves of an ECG signal. This does not, however, limit the scope of the invention. In the case of an ECG type cardiac signal, a so-called RR series can also be constructed by using the other depolarisation waves (P, Q, S or T) of the ECG signal to construct the RR series, which, however, is less precise than when using the R waves of the ECG signal. Similarly, when the cardiac signal is not an ECG signal, the samples of the RR series are not calculated by determining the time interval separating two successive R waves of the ECG signal, but they are instead determined in a more general manner by measuring, in the cardiac signal, the time interval between two successive heart beats.

The final parameter calculated by means of the method or the system according to the invention enables in a general manner the characterisation of any stimulus affecting ANS activity and resulting in a variation of cardiac rhythm (or frequency).

A first important application of the invention is found in the medical or surgical domain, to assess the level of pain in a living being.

In the medical or surgical domain, it is indeed important to have knowledge of the level of pain felt by a patient, in order in particular to be able to allow for and provide the best possible treatment for said pain.

The most widespread pain assessment method to date is a subjective method, based on the use of a sliding scale allowing the patient to indicate by means of a cursor or equivalent the level of pain felt on a pre-established pain scale. This method has the disadvantage, on the one hand, of being completely subjective and therefore not totally reliable and, on the other hand, of being suitable for use only with conscious patients.

Furthermore, in the case of a conscious patient under local anaesthesia, such as a patient under epidural anaesthesia, for instance, the above-described subjective assessment method cannot be used for the automatic control in real time of the administration of anaesthetic agents.

It is also of interest in the domain of general anaesthesia to be able to know the level of pain felt by the unconscious patient. The knowledge of said level of pain enables the best possible adaptation of the administration of analgesic agents.

For the above-described reasons, there is significant interest in proposing an objective method for assessing the pain felt by a living being, said method needing to result in the automatic calculation of a parameter measuring the level of pain.

The present invention thus has as its other objects the use of the above-described analysis system as well as the application of the above-described method of analysing the variability of the cardiac rhythm, for the assessment of the pain felt by a living being, the final calculated parameter characterising the level of pain.

Depending on context, according to the invention, pain assessment can be carried out as the case may be on a conscious living being who is not being mechanically ventilated (i.e. a living being whose respiratory frequency is normal and variable and not dictated by a controlled ventilation device, in contrast in particular with a patient under general anaesthesia) as well as on an unconscious living being, in particular a living being under general anaesthesia. In the latter case (a living being under general anaesthesia), the assessment of the level of pain provides indirect knowledge on the level of analgesia during general anaesthesia.

A second important application of the invention can be found in the paramedical domain, for assessing the level of stress in a living being.

DESCRIPTION OF THE DRAWINGS

Other characteristics and advantages of the invention will appear more clearly upon reading the detailed description of a non-limiting and non-exhaustive example and with reference to the accompanying drawings, in which.

DETAILED DESCRIPTION

Analysis System of the Variability of the Cardiac Rhythm

Figure 1:
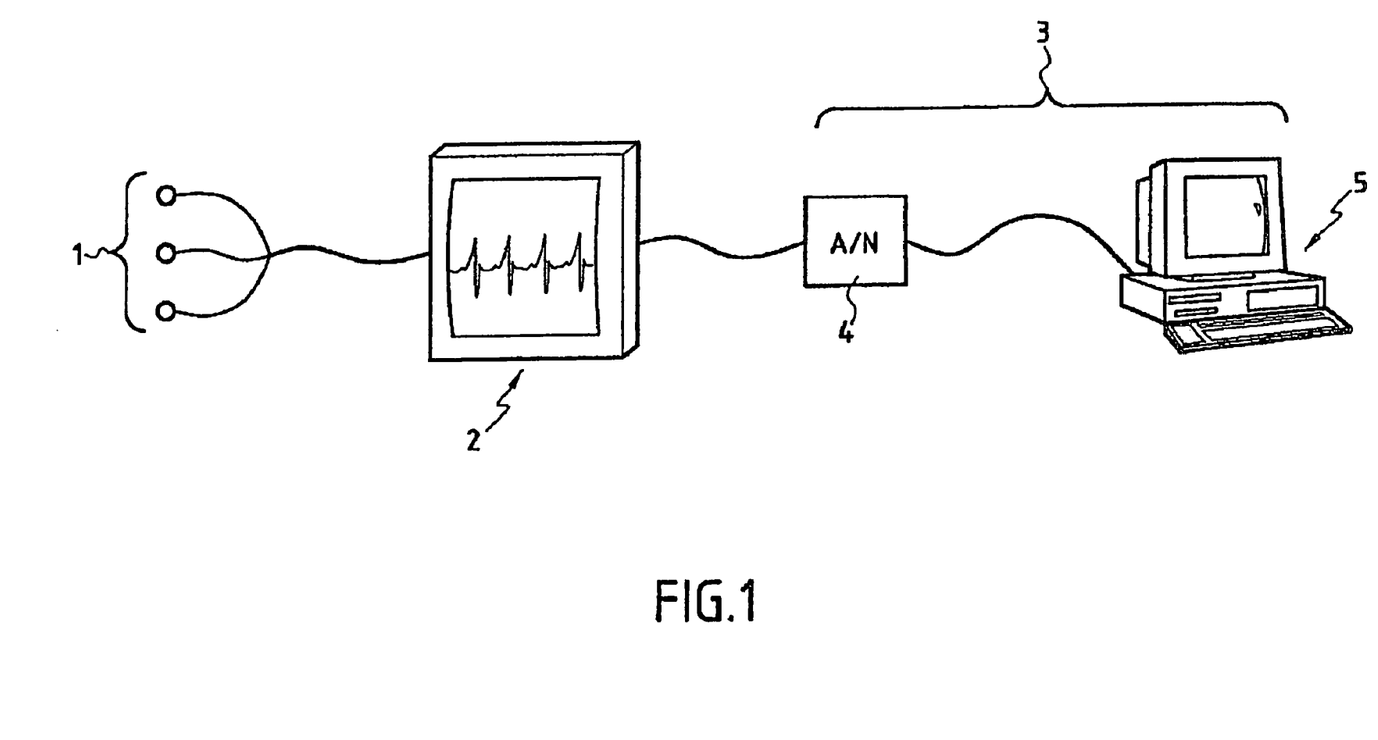
FIG. 1 shows a diagram of the main elements of an example of an analysis system according to the invention.

FIG. 1 shows an example of an analysis system of the variability of the cardiac rhythm enabling the acquiring and processing of the cardiac signal of a living being (hereinafter referred to as "patient") in accordance with the invention.

This system comprises:
- conventional means for acquiring an ECG signal, comprising several measurement electrodes 1 connected to the input of an electrocardiographic (ECG) monitor 2,
- means 3 for processing the ECG signal provided by the output of the ECG monitor 2.

The processing means 3 of the ECG signal comprise an analogue-to-digital converter 4 and a programmed processing unit 5. The input of the converter 4 is connected to the output of the ECG monitor 2, and the output of the converter 4 is connected to an input port of the processing unit 5. In a particular non-limiting embodiment of the invention, the processing unit 5 consists of a microcomputer, with the converter 4 being connected to a communication port of said microcomputer (an RS232 serial port or USB port, for instance).

Figure 2:
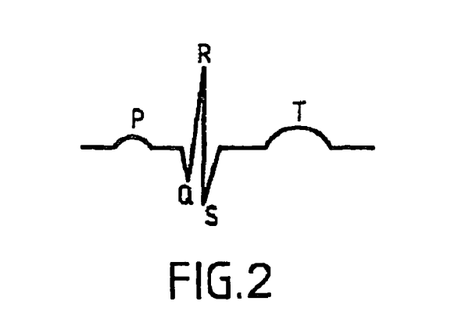
FIG. 2 shows the set of waves (PQRST) characteristic of a heart beat in an ECG signal.

In operating mode, the electrodes 1 are applied to the body of a patient and the ECG monitor in a conventional manner outputs an analogue electrical signal, called an ECG signal, which, for each heart beat, has the form of the signal shown in FIG. 2, for instance.

In reference to FIG. 2, for each heart beat, this electrocardiographic (ECG) signal consists of a set of electrical waves:
- the P wave, which corresponds to the depolarisation of the atria and which presents a low amplitude and a dome form;
- the PQ space, which represents the atrioventricular conduction time;
- the R wave, considered in practice as a marker of ventricular systole, or of the heart beat, the QRS complex reflecting ventricular contraction, and
- the T wave, which reflects ventricular repolarisation.

This analogue ECG signal is digitised by the converter 4, at a predefined sampling frequency (fc) of a value of 256 Hz, for instance.

Figure 3:
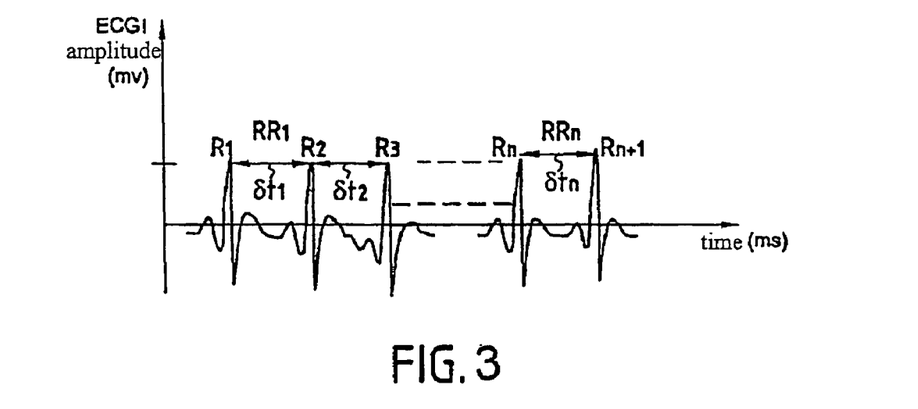
FIG. 3 shows an example of a digital ECG signal, obtained after sampling an analogue ECG signal.

The sampled signal provided by the output of the converter 4 (signal shown in FIG. 3) is processed by the processing unit 5, by means of specific processing software (pain assessment software), described in more detail below. This pain assessment software is stored in the memory of the processing unit 5 and, when executed, enables the automatic calculation, from the digital signal delivered by the analogue-to-digital converter 4, of two distinct parameters (AUCmax and AUCmoy) measuring the level of pain of a patient.

A preferred variation of this pain assessment software is described in more detail hereinafter.

Algorithm Example of Pain Assessment Software

In a preferred embodiment of the invention, the main successive stages of the algorithm of the pain assessment software are the following:
1. Acquisition of RRi samples and re-sampling at a predetermined frequency f
2. Selection of RRi samples comprised in a main time window of n seconds (n>1/f)
3. Filtering
4. Normalisation of signal
5. Measurement of minima (Pi) in main window
6. Cutting of main time window into m [m≧2] subwindows ($F_j$) and calculation for each subwindow ($F_j$) of area ($A_j$), delimited by the lower envelope ($C_j$) linking the minima (Pi) measured in the previous stage
7. Calculation of AUCmoy and AUCmax parameters
8. Shifting, by a time interval measuring p seconds (p≦n), of the main time window by n seconds, and repeating the stage 2 calculation.

In practice, the system can be programmed to be used in real time or in deferred time.

When the system is used in deferred time, stage 1 is, in a first instance, performed in real time so as to obtain all the RRi samples for the entire desired analysis period; these successive RRi samples are then stored in their entirety in an acquisition file in the processing unit's memory. In a second instance, stages 2 to 8 are carried out in a continuous loop, in deferred time, using the RRi interval values stored in the acquisition file.

When the system operates in real time, on the one hand, the acquisition stage 1 and, on the other hand, the subsequent processing stages 2 to 8 are carried out by two distinct software modules running in parallel, the first acquisition module (stage 1) feeding the second processing and calculation module (stages 2 to 8) by means of a buffer file or equivalent.

Stages 1 to 8 are detailed hereinafter:

Stage 1: Acquisition of RRi Samples and Re-sampling at a Predetermined Frequency f The acquisition of RRi samples is carried out by a first software sub-module which receives as input successive digital data constituting the digital ECG signal (signal of FIG. 3) provided by the analogue-to-digital converter 4. Each piece of data (or point) of the ECG signal is defined by the instantaneous amplitude $ECG_i$ of the ECG signal and by the sampling instant $t_i$ ($t_i = n_i/fc$, with $n_i$ being the sample number and fc representing the sampling frequency of the converter 4).

The first sub-module for the acquisition of the RRi samples is designed to measure automatically each successive Ri peak in the digital signal provided by the converter 4 and to construct automatically an RR series (FIG. 4) consisting of a succession of $RR_j$ samples. Each $RR_j$ sample is defined by the following pair of coordinates: ti [sampling instant (or number)], time interval δti (expressed in multiples of the sampling period fc, for instance) separating a peak $R_j$ from the following peak $R_{j+1}$ (in another variation this can also apply to the previous peak $R_{j-1}$).

Figure 4:
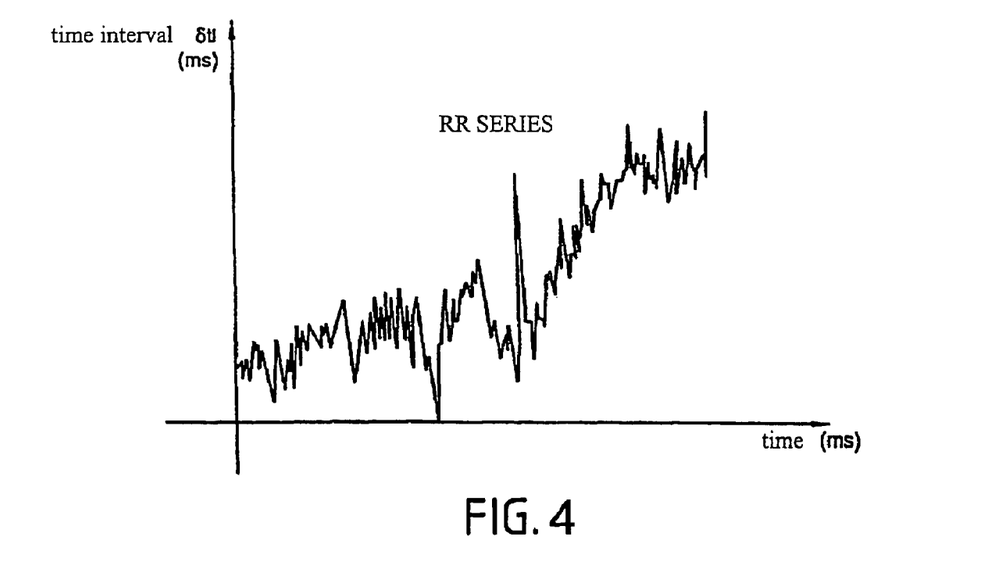
FIG. 4 shows an example of an RR series (also called RR signal) constructed from the signal of FIG. 3.

Since the R wave is conventionally the narrowest portion with the highest amplitude of the QRS complex, it is the wave preferably used to measure the heart beat with a very high precision, the time interval δti corresponding in practice to the time separating two successive heart beats. Nevertheless, in another variation, one could foresee using other waves (for instance, the Q wave or the S wave) of a heart beat of the ECG signal to measure and construct the RR series.

The RR series (FIG. 4) provided by the above-described first sub-module is automatically re-sampled by a second software sub-module at a predefined frequency f. This re-sampling frequency f must be superior to double the maximum physiological cardiac frequency of the patient. In order to take into account all the possible physiological situations, the re-sampling frequency f is preferably fixed at a value superior to 6 Hz.

The object of this re-sampling is to output an RR series in which the $RR_i$ samples are equidistant from a temporal point of view, i.e. in other words an RR series in which the sampling instants are regular. This re-sampling is carried out in the known manner by interpolation, for instance by linear interpolation.

Stage 2: Selection of RRi Samples Comprised in a Main Time Window of n Seconds (n>1/f)

This stage consists in isolating a number N of successive RRi samples (N=n.f). As a rough guide, a main window of 64 seconds (n=64) is selected for example, corresponding to 512 successive RRi samples (N=512), with a re-sampling frequency f of 8 Hz.

The following stages 3 to 7 are applied to the samples comprised in this main window.

Stage 3: Filtering/[f1; f2]

This stage consists in applying a bandpass filter on the samples of the RR series comprised in the main window, so as to keep only the frequencies lying within a predefined frequency bandwidth [f1; f2].

e particularly, the frequency bandwidth [f1; f2] is equal to or lying within the frequency band [0.05 Hz; 5 Hz]. The frequency bandwidth [f1; f2] is preferably equal to [0.1 Hz; 1 Hz].

To implement this stage of bandpass filtering, a digital high-pass filter is used, for instance, having a cut-off frequency at frequency f1, connected in series with a digital low-pass filter having a cut-off frequency at frequency f2. It is also possible to use a recursive selective filter with an infinite impulse response (IIR filter) centred on the frequency bandwidth [f1; f2].

The high-pass filter (cut-off frequency f1) has as its objective the filtering of low frequencies inferior to 0.1 Hz and simultaneously the removing of numerous artefacts in the signal. In practice, the cut-off frequency f1 is thus superior or equal to 0.1 Hz and preferably lies within between 0.1 Hz and 0.15 Hz. It also has the advantage of being able to remove the average value of the signal. It is possible to omit the use of the high-pass filter. In this case, it is preferable, before calculating intermediary parameters $(A_j)$, to re-centre the signal to its average.

The low-pass filter (cut-off frequency f2) has as its objective the filtering of high frequencies, typically superior to 1 Hz, since in practice these do not contain any interesting information. The implementation of this low-pass filter, while preferred, is nevertheless optional and not indispensable for the implementation of the invention.

Stage 4: Normalisation of Signal

This stage is carried out by means of a software sub-module which in a first instance calculates the norm S of the signal resulting from stage 3 in accordance with the following commonly used formula:

$$S = \sqrt[p]{\sum_{i=1}^{N} (s_i)^p}$$

in which p is an integer superior to 1 and $S_i$ the discrete values of the signal.

In another variation, the norm can also be calculated by means of the following formula:

$$S = \frac{\sqrt[p]{\sum_{i=1}^{N} (s_i)^p}}{N}$$

Preferably, for the implementation of the invention, p will be chosen equal to 2.

In a second instance, the software sub-module performs a normalisation of the signal by dividing each value $S_i$ of the signal by the norm S previously calculated.

This stage 4 enables procurement of a better sensitivity regarding the final result (sensitivity of AUCmoy and AUCmax parameters measuring the level of pain).

It is essential that this normalisation be carried out on the entire width of the main window, i.e. taking into account, during normalisation, the (N) RRi samples of the main window. In contrast, a normalisation performed on each subwindow $(A_j)$ would be completely futile.

Stage 5: Measurement of Minima in Main Window

Figure 5:
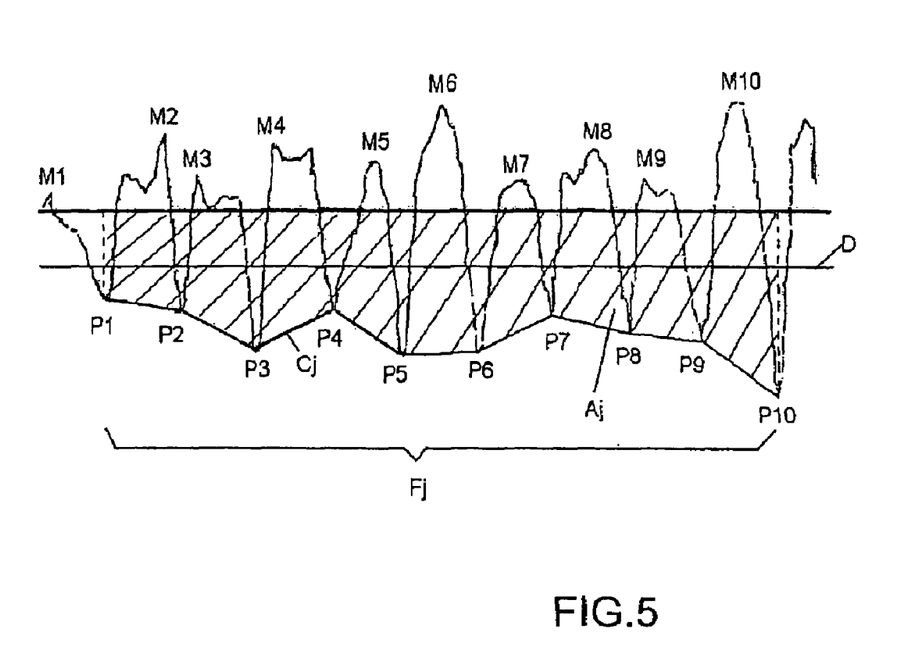
FIG. 5 shows an example of an RR series after filtering and normalisation.

FIG. 5 shows an RR signal example (after filtering and normalisation) obtained in the above-described stage 4. In this Figure, the abscissa axis corresponds to the zero value of the filtered and normalised signal.

Stage 5 is carried out by means of a software sub-module, which measures the minima (points $P_i$ on FIG. 5) of this signal, for instance by means of an algorithm measuring an inversion of the gradient (or, in an equivalent manner, a change in the sign of the signal derivative).

Stage 6: Cutting of the main time window into m [m≧2] subwindows $(F_j)$ and calculation for each subwindow $(F_j)$ of area $(A_j)$, delimited by the lower envelope $(C_j)$ linking the minima measured in the previous stage The software sub-module corresponding to stage 6 automatically calculates, for each subwindow $(F_j)$, a lower envelope (curve $C_j$ in FIG. 5), which links the minima (points $P_i$) measured in stage 5 and comprised in the subwindow $(F_j)$. This lower envelope $(C_j)$ is for instance determined by linear interpolation, i.e. by calculating the straight line segments linking the minimum points $(P_i)$.

Following this, the software sub-module corresponding to stage 6 calculates, for each subwindow $(F_j)$, the area $(A_j)$, delimited by the lower envelope $(C_j)$ and the abscissa axis (signal zero value). The area $(A_j)$ corresponds to the hatched area of FIG. 5.

When the lower envelope $(C_j)$ is approximated by straight line segments, this calculation of area $(A_j)$ involves calculating the sum of the trapeze areas delimited by two successive minimum points $(P_i)$ and the abscissa axis.

In an alternative embodiment, the area $(A_j)$ could be delimited by the lower envelope $(C_j)$ and a horizontal straight line differing from the abscissa axis and preferably (but not necessarily) positioned below the abscissa axis, as for instance the dotted straight line D of FIG. 5. Similarly, in another embodiment, this straight line D for the calculation of the area $(A_j)$ could be positioned above the abscissa axis, and in particular pass through point Mi of the highest ordinate value (point M10 in the specific example of FIG. 5).

As a non-limiting example, the method has been tested with a main window time of 64s and, for the implementation of stage 6, this main window was cut into four (m=4) subwindows $F_1$ to $F_4$ of 16s.

Stage 7: Calculation of AUCmoy and AUCmax Parameters

The two AUCmoy and AUCmax parameters enable the measurement of the level of pain.

AUCmoy is equal (or more generally proportional) to the average of the areas Aj of the (m) subwindows $F_j$.

AUCmax is equal (or more generally proportional) to the greatest value of the areas Aj calculated for the (m) subwindows $F_j$.

Stage 8: Shifting, by a time interval measuring p seconds ($p \leq n$), of the time window by n seconds, and repeating the stage 2 calculation.

The step (p) for the sliding of the main calculation window and the repetition of stages 2 to 8 has an influence on the sensitivity of the AUCmoy and AUCmax parameters and is thus dependent on the sought after sensitivity. As a rough guide, and in practice, highly satisfying results have been obtained when selecting a step (p) measuring 2 s.

In a further embodiment, the above-described filtering stage (stage 3) could be carried out before the selection stage 2, for instance in a continuous manner as and when RRi samples are acquired. Similarly, in another variant implementation, this filtering stage could be carried out after the normalisation stage (stage 4 described above).

Experimental Validation

Tests have shown that the AUCmoy parameter and the AUCmax parameter were each correlated to the intensity of the painful stimulus felt by a living being, these parameters thus enabling the measurement of the intensity of pain in a living being.

In order to validate this correlation between the above-described AUCmoy and AUCmax parameters and the experienced level of pain, these AUCmoy and AUCmax parameters were tested on a population of adult parturients, with no history of cardiovascular disease, diabetes or neurological disorders, classed as ASA I or II, due to give birth at full-term by vaginal delivery under epidural analgesia (EA).

The calculated AUCmoy and AUCmax values were compared with the indications of pain levels provided by the parturients by means of an analogue visual pain scale (EVA), both before the placement of an epidural and after the placement of an epidural.

This comparison made it possible to demonstrate that the AUCmoy and AUCmax parameters were correlated with the indications of pain levels provided by the parturients by means of the EVA.

It is particularly noticeable that the AUCmax parameter is the most reliable, and thus preferential, parameter.

The two AUCmoy and AUCmax parameters were tested on conscious patients and it was possible to determine that, in an advantageous manner according to the invention, these parameters are independent of the living being's own respiratory frequency.

The two AUCmoy and AUCmax parameters were also successfully tested for the assessment of pain on unconscious patients under general anaesthesia, whose respiratory frequency was ruled by a controlled ventilation mechanism. Knowing these parameters during general anaesthesia enables an indirect measurement of the analgesic component during general anaesthesia.

The invention is not, however, limited to the two specific, above-described AUCmoy and AUCmax parameters that were given only as preferred examples.

More generally, it has been found that an essential element of the invention influencing the targeted result (assessment of pain) is the calculation of a final parameter from the intermediary parameters calculated on the RRi samples comprised in time subwindows, in contrast with a solution (not part of the invention) in which the final parameter would be calculated directly from the set of RRi samples of the main window in their entirety. In general, the method of the invention could thus be implemented with any method of processing RRi samples enabling the calculation of an intermediary parameter Aj in time subwindows, the final parameter being correlated with the intensity of the pain stimulus, in function of these intermediary parameters.

Similarly, it has been demonstrated that, unexpectedly, the pain stimulus very noticeably influenced the respiratory peaks (minimum points Pi); the more intense the pain stimulus, the weaker the amplitude of the peaks in the signal corresponding to the minima (Pi), which in some cases can be practically zero. In contrast, the maxima (Mi) of the curve are not noticeably influenced by the pain stimulus. Consequently, any method of processing RRi samples in each subwindow (Fj), which enables the taking into account of the amplitude variations of these peaks (Pi), will be appropriate for calculating the intermediary parameters in each subwindow, and the invention is thus not limited to the calculation of the area described above and given only as an example. As a non-exhaustive example, the calculation of the areas (Aj) could be replaced by the calculation of an intermediary parameter in function of the amplitudes of the peaks corresponding to the minimum points (Pi). Similarly, in a further embodiment, it is possible to calculate each intermediary parameter ($A_j$) by applying on the RRi samples of the subwindow ($F_j$) a wavelet transform, based on a wavelet of an appropriate form (for instance, Daubechies wavelet).

In the embodiments, which have been described with reference to the accompanying drawings, the calculation algorithms are applied to an RR series of which the samples (RRi) characterise the time intervals ($\delta$ti) separating two successive heart beats. In another embodiment, the invention can be implemented on the basis of an RR series of which the samples (RRi) characterise the inverse (1/$\delta$ti) of the time intervals ($\delta$ti) between two successive heart beats. In this case, by applying the above-described stages 1 to 4, a curve inverse to that of FIG. 5 is obtained, points Pi becoming maxima and points Mi becoming minima, and the calculation of the areas (Aj) described above (stage 6) is carried out based on a higher envelope (Cj) linking the maximum points (Pi).

The calculation algorithm described in detail above, as well as the parameters that ensue from it, namely the AUCmoy and AUCmax parameters, are not limited in terms of application to the assessment of pain in a living being but can, in a more general manner, be used to measure the variability of cardiac rhythm in a living being (conscious or unconscious) and, as a result, to study the effects on the ANS (Autonomic Nervous System) of any stimulus likely to modify the activity of the ANS.

Thus, the above-described instruction applied to the assessment of pain can also be used and transferred as it stands to other domains of application and in particular to the paramedical domain, to assess the stress levels felt by a living being (conscious or unconscious).

The invention claimed is:

1. A method for processing an RR series using a processing unit, the RR series consisting of a plurality of samples, each sample representing the time intervals separating two successive heart beats or the inverse of said time intervals, said method comprising:

selecting samples in a main time window having a predetermined length of time;

cutting said main window into subwindows;

calculating an intermediary parameter for each subwindow on the basis of the samples contained in the subwindow; and calculating a final parameter as a function of the intermediary parameters.

2. Method according to claim 1, wherein the final parameter is calculated by iteration, by shifting the main time window by a predetermined time interval less than the length of time of the main window.

3. Method according to claim 1, wherein each intermediary parameter is a function at least of the minima of the RR series in the subwindow when the samples of the series represent the time intervals separating two successive heart beats, or is a function at least of the maxima of the RR series in the subwindow when the samples of the series represent the inverse of the time intervals separating two successive heart beats.

4. Method according to claim 1, wherein the calculated value for the final parameter is proportional to the maximum value of the intermediary parameters.

5. Method according to claim 1, wherein the calculated value for the final parameter is proportional to the average value of the intermediary parameters.

6. Method according to claim 1, wherein, for the calculation of the intermediary parameters, an envelope is defined, linking the minimum points measured when the samples of the series represent the time intervals separating two successive heart beats, or linking the maximum points measured when the samples of the series represent the inverse of the time intervals separating two successive heart beats.

7. Method according to claim 6, wherein each intermediary parameter is a function of an area delimited by the envelope.

8. Method according to claim 1, wherein, prior to the calculation of the intermediary parameters, the RR series is filtered by means of a high-pass filter with a cut-off frequency superior or equal to 0.1 Hz.

9. Method according to claim 1, wherein, prior to the calculation of the intermediary parameters, in each subwindow, the samples of the RR series are normalised over the entire width of the main window.

10. A system for analysing the variability of a cardiac rhythm, said system comprising:
means of acquiring an analogue cardiac signal;
means of sampling said cardiac signal; and
means of processing the sampled signal, designed to construct an RR series consisting of a plurality of samples, each sample representing the time intervals separating two successive heart beats or the inverse of said time intervals, wherein said processing means are furthermore designed to calculate automatically from the series at least one final parameter by selecting samples in a main time window having a predetermined length of time, cutting said main window into subwindows, calculating an intermediary parameter for each subwindow on the basis of the samples contained in the subwindow, and calculating said at least one final parameter as a function of the intermediary parameters.

11. System according to claim 10 for the assessment of pain, the final calculated parameter characterising a level of pain.

12. System according to claim 10 for the assessment of stress, the final calculated parameter characterising a level of stress.

13. System according to claim 10 for the assessment of pain felt by a living being.

14. System according to claim 10 for the assessment of stress felt by a living being.

15. A method for analysing the variability of the cardiac rhythm of a living being, said method comprising:
acquisition of an analogue cardiac signal of the living being;
sampling of using an analog-to-digital converter to sample said cardiac signal and construct of an RR series consisting of a plurality of samples, each sample representing the time intervals that separate two successive heart beats or the inverse of said time intervals; and
processing of the RR series using a processing unit by selecting samples in a main time window having a predetermined length of time, cutting said main window into subwindows, calculating an intermediary parameter for each subwindow on the basis of the samples contained in the subwindow, and calculating a final parameter as a function of the intermediary parameters.

16. Method according to claim 15 for the assessment of the pain felt by a living being, the final calculated parameter characterising the level of pain.

17. Method according to claim 15 for the assessment of the stress felt by a living being, the final calculated parameter characterising the level of stress.

18. Method according to claim 1, wherein, prior to the calculation of the intermediary parameters, the RR series is filtered by means of a high-pass filter with a cut-off frequency between 0.1 Hz and 0.15 Hz.

* * * * *

UNITED STATES PATENT AND TRADEMARK OFFICE
CERTIFICATE OF CORRECTION

PATENT NO. : 8,352,020 B2  
APPLICATION NO. : 11/663166  
DATED : January 8, 2013  
INVENTOR(S) : Regis Logier et al.

Page 1 of 1

It is certified that error appears in the above-identified patent and that said Letters Patent is hereby corrected as shown below:

In the Specifications:

Column 7, line 29, "e particularly," should be --More particularly,--.

Column 8, line 38, after "stage" insert --.--.

In the Claims:

Column 12, line 25, Claim 15, after "construct" delete "of".

Signed and Sealed this  
Fourth Day of June, 2013

Teresa Stanek Rea  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,352,020 B2 | Page 1 of 1 |
| APPLICATION NO. | : 11/663166 | |
| DATED | : January 8, 2013 | |
| INVENTOR(S) | : Logier et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1017 days.

Signed and Sealed this
Twenty-sixth Day of August, 2014

Michelle K. Lee
*Deputy Director of the United States Patent and Trademark Office*